United States Patent
Miyazaki

(10) Patent No.: US 10,684,343 B2
(45) Date of Patent: Jun. 16, 2020

(54) MAGNETIC RESONANCE IMAGING APPARATUS AND MAGNETIC RESONANCE IMAGING METHOD

(71) Applicant: Toshiba Medical Systems Corporation, Otawara-shi (JP)

(72) Inventor: Mitsue Miyazaki, Otawara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 143 days.

(21) Appl. No.: 15/609,733

(22) Filed: May 31, 2017

(65) Prior Publication Data

US 2018/0348326 A1  Dec. 6, 2018

(51) Int. Cl.
| | | |
|---|---|---|
| *G01R 33/563* | (2006.01) | |
| *G01R 33/56* | (2006.01) | |
| *A61B 5/055* | (2006.01) | |
| *G01R 33/54* | (2006.01) | |
| *G01R 33/567* | (2006.01) | |
| *G01R 33/483* | (2006.01) | |

(52) U.S. Cl.
CPC ..... *G01R 33/5635* (2013.01); *G01R 33/5607* (2013.01); *A61B 5/055* (2013.01); *G01R 33/4835* (2013.01); *G01R 33/546* (2013.01); *G01R 33/5673* (2013.01); *G06T 2207/10088* (2013.01)

(58) Field of Classification Search
CPC ........... G01R 33/5635; G01R 33/5607; G01R 33/5673; G01R 33/546; G01R 33/483; G01R 33/4833–4836; A61B 5/055; G06T 2207/10088

USPC ........................................................ 324/309
See application file for complete search history.

(56) References Cited

U.S. PATENT DOCUMENTS

| 5,560,360 | A  | * | 10/1996 | Filler | G01R 33/56341 324/307 |
|---|---|---|---|---|---|
| 6,782,286 | B2 | * | 8/2004 | Miyazaki | G01R 33/563 324/306 |
| 7,323,871 | B2 | * | 1/2008 | Foo | G01R 33/4828 324/307 |
| 8,115,485 | B1 | * | 2/2012 | Maier | G01R 33/543 324/307 |
| 2002/0188190 | A1 | * | 12/2002 | Kassai | A61B 5/7285 600/410 |

(Continued)

FOREIGN PATENT DOCUMENTS

JP    2009-160052 A    7/2009

*Primary Examiner* — Patrick Assouad
*Assistant Examiner* — Demetrius R Pretlow
(74) *Attorney, Agent, or Firm* — Oblon, McClelland, Maier & Neustadt, L.L.P.

(57) ABSTRACT

A magnetic resonance imaging apparatus according to an embodiment includes sequence control circuitry and processing circuitry. The sequence control circuitry executes two pulse sequences, thereby acquiring two pieces of data, each of the two pulse sequences being a pulse sequence in which the sequence control circuitry acquires data after applying a short inversion time recovery (STIR) pulse while concurrently applying a gradient magnetic field for spatial selection and each of the two pulse sequences being executed in two different timings by the sequence control circuitry. The processing circuitry generates an image by performing a subtraction processing between the two pieces of data acquired by the sequence control circuitry.

5 Claims, 10 Drawing Sheets

(56) References Cited

U.S. PATENT DOCUMENTS

| | | | |
|---|---|---|---|
| 2007/0007958 A1* | 1/2007 | Foo | G01R 33/4828 324/307 |
| 2007/0069724 A1* | 3/2007 | Zhao | G01R 33/4818 324/306 |
| 2007/0080685 A1* | 4/2007 | Bydder | G01R 33/561 324/309 |
| 2008/0048657 A1* | 2/2008 | Reeder | G01R 33/4828 324/309 |
| 2008/0081986 A1* | 4/2008 | Slavin | A61B 5/055 600/410 |
| 2008/0238421 A1* | 10/2008 | Kitane | G01R 33/4828 324/307 |
| 2010/0268066 A1* | 10/2010 | Rehwald | A61B 5/055 600/419 |
| 2012/0116206 A1* | 5/2012 | Miyazaki | G01R 33/5635 600/410 |
| 2012/0116207 A1* | 5/2012 | Miyazaki | G01R 33/5635 600/410 |
| 2012/0283549 A1* | 11/2012 | Miyazaki | G01R 33/5673 600/413 |
| 2013/0208969 A1* | 8/2013 | Bashir | G06T 7/0012 382/131 |
| 2014/0084922 A1* | 3/2014 | Fu | G01R 33/5607 324/309 |
| 2016/0047871 A1* | 2/2016 | Zhou | G01R 33/5635 324/309 |
| 2016/0139222 A1* | 5/2016 | Frydman | G01R 33/483 324/309 |
| 2016/0154081 A1* | 6/2016 | Chung | G01R 33/56563 324/309 |
| 2017/0108567 A1* | 4/2017 | Bhat | G01R 33/5602 |
| 2018/0110424 A1* | 4/2018 | Giri | A61B 5/0263 |

\* cited by examiner

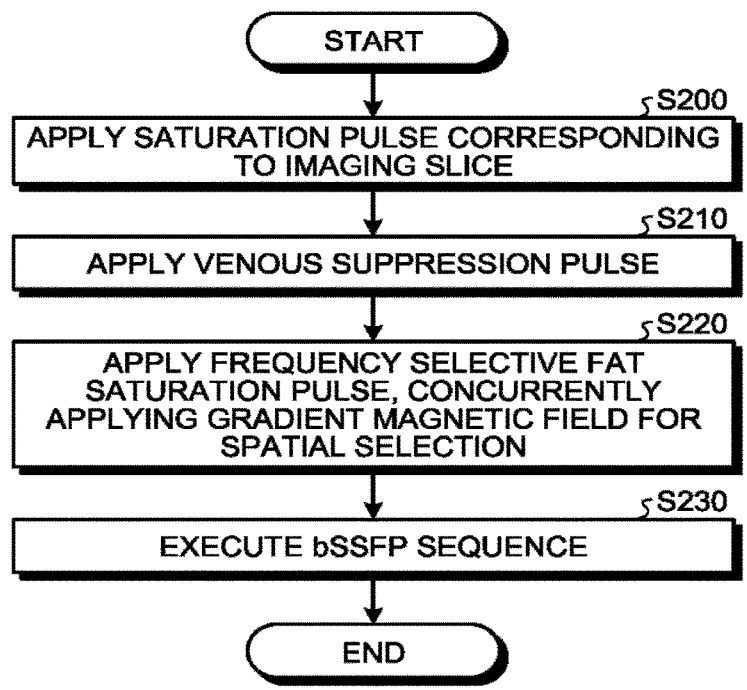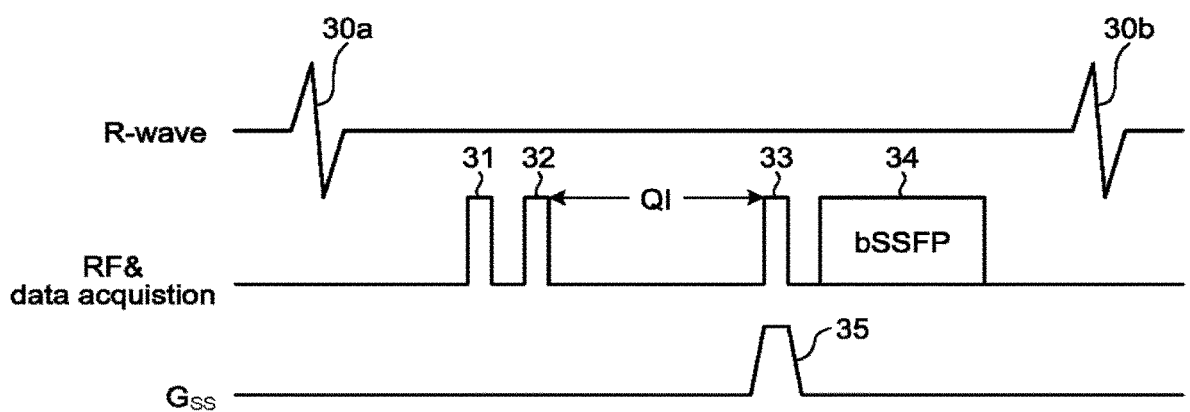

MAGNETIC RESONANCE IMAGING APPARATUS AND MAGNETIC RESONANCE IMAGING METHOD

FIELD

Embodiments described herein relate generally to a magnetic resonance imaging apparatus and a magnetic resonance imaging method.

BACKGROUND

A magnetic resonance imaging method capable of depicting flow of low velocity such as blood flow in the lower extremities without infusing a contrast agent includes fresh blood imaging (FBI) method. FBI method has an advantage that flow of lower velocity can be depicted well compared to other non-contrast methods, such as time-of-flight (TOF) method or phase contrast (PC) method. Further, FBI method has an advantage that images along the blood flow direction can be acquired with a fewer number of slices compared to TOF method or PC method.

In FBI method, pulse sequences are executed in two different cardiac phases, such as in the systolic phase and in the diastolic phase, thereby acquiring two pieces of data (two source images). Subsequently, subtraction processing is performed between the two pieces of data (two source images) acquired, thereby generating, for example, a subtraction image such as a subtraction maximum intensity projection (MIP) image.

However, in a case in which a disease such as stenosis is found in the subtraction image, for example, it is preferable that the details be observable by returning to the two source images, in which case it is preferable that fat suppression be already completed even in the source images.

However, an introduction of a short TI (inversion time) inversion recovery (STIR) pulse for fat suppression in accordance with a normal method sometimes renders blood signals inconspicuous.

BRIEF DESCRIPTION OF THE DRAWINGS

FIG. 9 is a flowchart illustrating a processing performed by a magnetic resonance imaging apparatus according to the second embodiment;

FIG. 10 is a diagram illustrating a pulse sequence executed by a magnetic resonance imaging apparatus according to the second embodiment;

DETAILED DESCRIPTION

A magnetic resonance imaging apparatus according to an embodiment includes sequence control circuitry and processing circuitry. The sequence control circuitry executes two pulse sequences, thereby acquiring two pieces of data, each of the two pulse sequences being a pulse sequence in which the sequence control circuitry acquires data after applying a short inversion time recovery (STIR) pulse while concurrently applying a gradient magnetic field for spatial selection and each of the two pulse sequences being executed in two different timings by the sequence control circuitry. The processing circuitry generates an image by performing a subtraction processing between the two pieces of data acquired by the sequence control circuitry.

Hereafter, embodiments of the present invention are described with reference to the drawings. Common numeral signs are assigned to the same components in different figures and duplicated explanations are omitted.

First Embodiment

Figure 1:
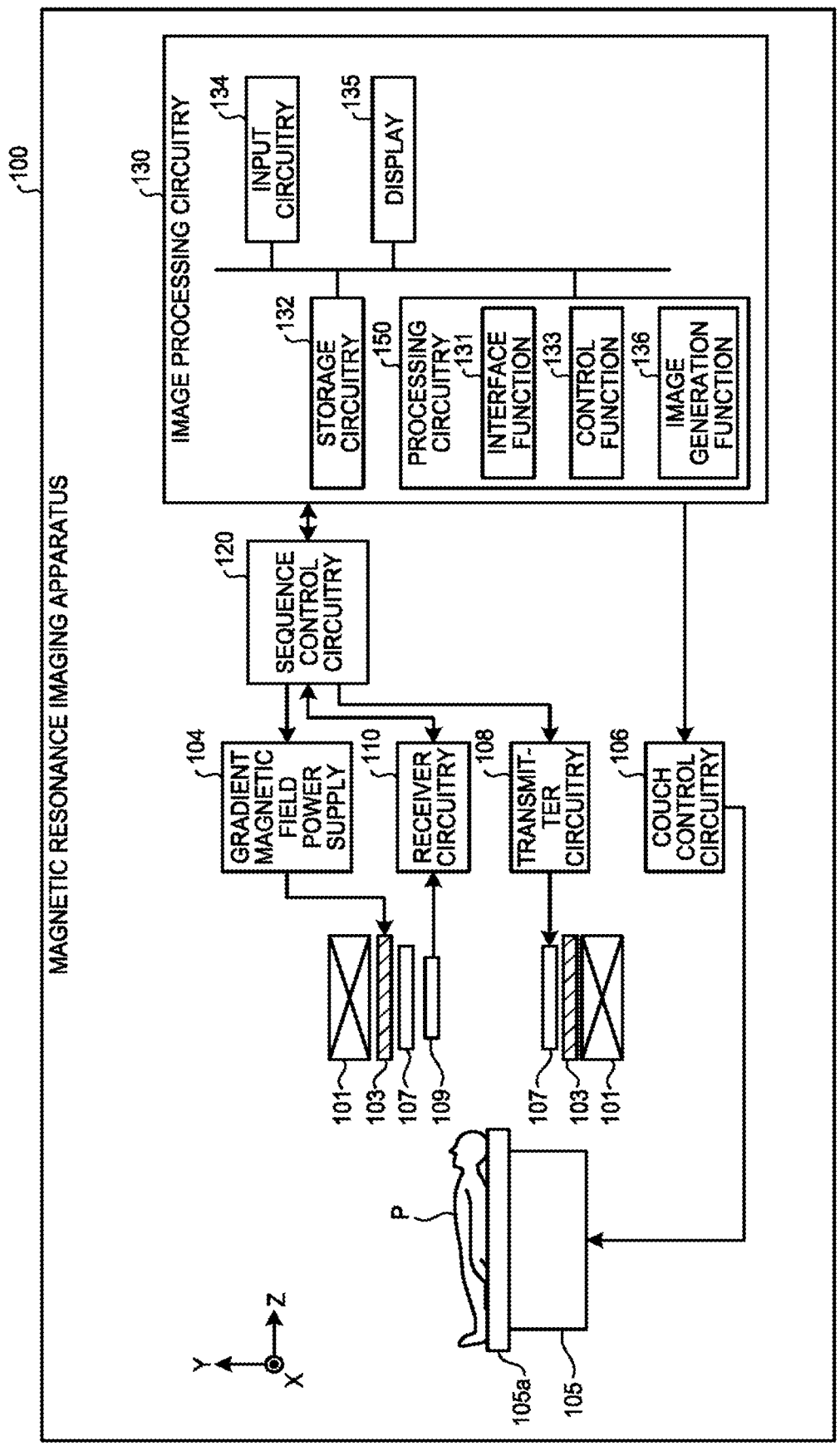
FIG. 1 is a diagram illustrating a magnetic resonance imaging apparatus according to an embodiment.

FIG. 1 is a block diagram of a magnetic resonance imaging apparatus 100 according to a first embodiment. As illustrated in FIG. 1, the magnetic resonance imaging apparatus 100 includes a static magnetic field magnet 101, a static magnetic field power source (not illustrated), a gradient coil 103, a gradient magnetic field power supply 104, a couch 105, couch control circuitry 106, a transmitter coil 107, transmitter circuitry 108, a receiver coil 109, receiver circuitry 110, sequence control circuitry 120, and an image processing apparatus 130. The magnetic resonance imaging apparatus 100 does not include an examined subject (such as a human body) P. The configuration illustrated in FIG. 1 is merely an example. In another example, any of the unit included in the sequence control circuitry 120 and the image processing apparatus 130 may be integrated together or separated, as appropriate.

The static magnetic field magnet 101 is a magnet formed in the shape of a substantially hollow circular cylinder and generates a static magnetic field in a space on an inside thereof. The static magnetic field magnet 101 may be configured by using, for example, a superconducting magnet and is magnetically excited by receiving supply of electric current from the static magnetic field power source. The static magnetic field power source supplies electric current to the static magnetic field magnet 101. Alternatively, the static magnetic field magnet 101 may be a permanent magnet, in which case the magnetic resonance imaging apparatus 100 need not comprise the static magnetic field power source. Further, the static magnetic field power source may be provided separately from the magnetic resonance imaging apparatus 100.

The gradient coil 103 is a coil formed in a shape of a substantially hollow circular cylinder and is disposed on an inside of the static magnetic field magnet 101. The gradient coil 103 is formed by combining three coils corresponding to X-, Y-, and Z-axes that are orthogonal to one another. These three coils individually receive supply of electric current from the gradient magnetic field power supply 104 and generate gradient magnetic fields of which the magnetic field intensities change along the X-, Y-, and Z-axes. The gradient magnetic fields on the X-, Y-, Z-axes that are generated by the gradient coil 103 correspond to, for example, a slice encode gradient magnetic field Gs, a phase encode gradient magnetic field Ge, and a readout gradient magnetic field Gr, respectively. The gradient magnetic field power supply 104 supplies the electric current to the gradient coil 103.

The couch 105 includes a couchtop 105a on which the subject P is placed. Under control of the couch control circuitry 106, while the subject P is placed thereon, the couchtop 105a is inserted into a hollow (i.e., an image taking opening) of the gradient coil 103. Normally, the couch 105 is provided so that a longitudinal direction thereof extends parallel to a central axis of the static magnetic field magnet 101. Under control of the image processing apparatus 130, the couch control circuitry 106 drives the couch 105 so that the couchtop 105a moves in longitudinal directions and in up-and-down directions.

The transmitter coil 107 is disposed on an inside of the gradient coil 103 and generates a radio frequency magnetic field by receiving a supply of a radio frequency (RF) pulse from the transmitter circuitry 108. The transmitter circuitry 108 supplies an RF pulse corresponding to Larmor frequency determined by a type of targeted atoms and magnetic field intensities, to the transmitter coil 107.

The receiver coil 109 is disposed on an inside of the gradient coil 103 and receives magnetic resonance signals (hereinafter, "MR signals", as necessary) emitted from the subject P subjected to an influence of a radio frequency magnetic field. Upon reception of magnetic resonance signals, the receiver coil 109 outputs the received magnetic resonance signals to the receiver circuitry 110.

The transmitter coil 107 and the receiver coil 109 described above are mere examples. The configuration thereof may be realized by selecting one of the following or combining together two or more of the following: a coil having only a transmission function; a coil having only a reception function; and a coil having transmission and reception functions.

The receiver circuitry 110 detects the magnetic resonance signals output from the receiver coil 109 and generates magnetic resonance data based on the detected magnetic resonance signals. More specifically, the receiver circuitry 110 generates the magnetic resonance data by applying a digital conversion to the magnetic resonance signals output from the receiver coil 109. Further, the receiver circuitry 110 transmits the generated magnetic resonance data to the sequence control circuitry 120. The receiver circuitry 110 may be provided on a gantry device side where the static magnetic field magnet 101, the gradient coil 103, and the like are provided.

The sequence control circuitry 120 images the subject P, by driving the gradient magnetic field power supply 104, the transmitter circuitry 108, and the receiver circuitry 110, on the basis of sequence information transmitted from the image processing apparatus 130. The sequence information is information that defines a procedure of the imaging. The sequence information defines: an intensity of electric current to be supplied from the gradient magnetic field power supply 104 to the gradient coil 103 and a timing with which electric current is to be supplied; an intensity of an RF pulse to be supplied by the transmitter circuitry 108 to the transmitter coil 107 and the timing with which an RF pulse is to be applied; a timing with which magnetic resonance signals are to be detected by the receiver circuitry 110, and the like. The sequence control circuitry 120 may be configured with an integrated circuit such as an Application Specific Integrated Circuit (ASIC) or a Field Programmable Gate Array (FPGA) or an electronic circuit such as a Central Processing Unit (CPU) or a Micro Processing Unit (MPU). It is noted that the details of the pulse sequences executed by the sequence control circuitry 120 will be described later.

Further, upon reception of magnetic resonance data from the receiver circuitry 110 as a result of imaging of the subject P by driving the gradient magnetic field power source 104, the transmitter circuitry 108, and the receiver circuitry 110, the sequence control circuitry 120 forwards the received magnetic resonance data to the image processing apparatus 130.

The image processing apparatus 130 exercises overall control of the magnetic resonance imaging apparatus 100, or generates an image, and the like. The image processing apparatus 130 comprises storage circuitry 132, input circuitry 134, a display 135 and processing circuitry 150. The processing circuitry 150 includes an interface function 131, a control function 133 and an image generation function 136.

In the first embodiment, each processing function carried out at the interface function 131, the control function 133, the image generation function 136, is stored in the storage circuitry 132 in a form of an executable program by a computer. The processing circuitry 150 is a processor realizing a function corresponding to each program by reading a program from the storage circuitry 132 and thereafter executing the program. In other words, the processing circuitry 150 in a state of having read each program has each function illustrated within the processing circuitry 150 in FIG. 1. It is noted that, in FIG. 1, it is explained that the single processing circuitry 150 realizes the processing function carried out at the interface function 131, the control function 133, or the image generation function 136. However, a plurality of independent processors may constitute the processing circuitry 150, each processor of the processing circuitry 150 executing its own program. In other words, each function described above may constitute a program and the single processing circuitry may execute each program. Alternatively, a specific function may be implemented in an independent program execution circuitry dedicated for the specific function.

Terminology "processor" used in the above explanation is meant to refer to, for example, CPU (Central Processing Unit), GPU (Graphical Processing Unit), or ASIC (Application Specific Integrated Circuit), circuitry such as programmable logic device (i.e. SPLD (Simple Programmable Logic Device), CPLD (Complex Programmable Logic Device) and FPGA (Field Programmable Gate Array). A processor reads and executes a program stored in the storage circuitry 132, thereby realizing the function.

Further, instead of being stored in the storage circuitry 132, a program may be constructed such that it is directly incorporated within circuitry of a processor. In that situation, the processor realizes a function by reading and executing the program incorporated within the circuitry. The couch control circuitry 106, the transmitter circuitry 108, the receiver circuitry 110 may be constructed as well, with a use of electronic circuits such as processors described above.

The processing circuitry 150 sends sequence information to the sequence control circuitry 120 by the interface function 131 and receives magnetic resonance data from the sequence control circuitry 120. Further, upon reception of the magnetic resonance data, the processing circuitry 150 stores the received magnetic resonance data into the storage circuitry 132 by the interface function 131. When receiving the magnetic resonance data, the processing circuitry 150 having the interface function 131 stores the received magnetic resonance data in the storage circuitry 132.

The magnetic resonance data stored in the storage circuitry 132 is arranged into a k-space by the control function 133. As a result, the storage circuitry 132 stores therein k-space data.

The storage circuitry 132 stores therein the magnetic resonance data received by the processing circuitry 150 that has the interface function 131, the k-space data arranged in the k-space by the processing circuitry 150 having the control function 133, image data generated by the processing circuitry 150 having the image generation function 136, and the like. For example, the storage circuitry 132 is configured by using a Random Access Memory (RAM), a semiconductor memory element such as a flash memory, a hard disk, an optical disc, and the like.

The input circuitry 134 receives various types of instructions and inputs of information from an operator. For example, the input circuitry 134 is a pointing device such as a mouse or a trackball, a selecting device such as a mode changing switch, or an input device such as a keyboard. Under the control of the processing circuitry 150 that has the control function 133, the display 135 displays Graphical User Interface (GUI) used for receiving an input of an image taking condition and an image generated by the processing circuitry 150 that has the image generation function 136, and the like. For example, the display 135 is a display device such as a liquid crystal display device.

The processing circuitry 150 exercises overall control of the magnetic resonance imaging apparatus 100 by the control function 133 and controls image capturing processing, image generation processing, image display processing, and the like. For example, the processing circuitry 150 that has the control function 133 receives an input of the image taking condition (e.g., an image taking parameter) via the GUI and generates sequence information according to the received image taking condition. Further, the processing circuitry 150 that has the control function 133 transmits the generated sequence information to the sequence control circuitry 120.

The processing circuitry 150 reads a k-space data from the storage circuitry 132 by the image generation function 136 and generates an image through a reconstructing process such as Fourier transform on the read k-space data.

Next, background regarding a magnetic resonance imaging apparatus according to an embodiment is briefly explained.

A magnetic resonance imaging method capable of depicting flow of low velocity such as blood flow in the lower extremities without infusing a contrast agent includes fresh blood imaging (FBI) method. FBI method has an advantage that flow of lower velocity can be depicted well compared to other non-contrast methods, such as time-of-flight (TOF) method or phase contrast (PC) method. Further, FBI method has an advantage that images along the blood flow direction can be acquired with a fewer number of slices compared to TOF method or PC method.

In FBI method, pulse sequences are executed in two different cardiac phases, such as in the systolic phase and in the diastolic phase, thereby acquiring two pieces of data (two source images). Subsequently, subtraction processing is performed between the two pieces of data (two source images) acquired, thereby generating, for example, a subtraction image such as a subtraction maximum intensity projection (MIP) image.

However, in a case in which a disease such as stenosis is found in the subtraction image, for example, it is preferable that the details be observable by returning to the two source images. Therefore, it is preferable that fat suppression be already completed even in the source images. Further, in a case in which the subject moves during the imaging, fat signals remain in the subtraction signal, which degrades images. Therefore, also in the case described above, it is preferable that fat suppression be already completed even in the source images.

As for fat suppression, for example, application of a frequency selective fat saturation pulse can be considered. However, in a method in which a frequency selective fat saturation pulse is applied, an exacting shimming becomes a prerequisite. In a case in which the imaging region is large, however, such as a case of a coronal imaging, it becomes laborious to perform a shimming. Therefore, it can be considered that a short TI (inversion time) inversion recovery (STIR) pulse is spatially non-selectively applied as the fat saturation pulse, in which case data acquisition is performed near the null point of fat signals.

However, in a case in which an STIR pulse is spatially non-selectively applied, the recovery of longitudinal magnetization can sometimes be imperfect because blood in the upstream region is spatially non-selectively excited by the STIR pulse but the repetition time (TR) is too short. Consequently, in a case in which an STIR pulse is spatially non-selectively applied, it becomes often the case that the blood signal becomes weak.

FIG. 2A to FIG. 2D illustrate this situation. FIG. 2A, FIG. 2B, FIG. 2C and FIG. 2D are drawings illustrating a background of an embodiment.

Figure 2A:
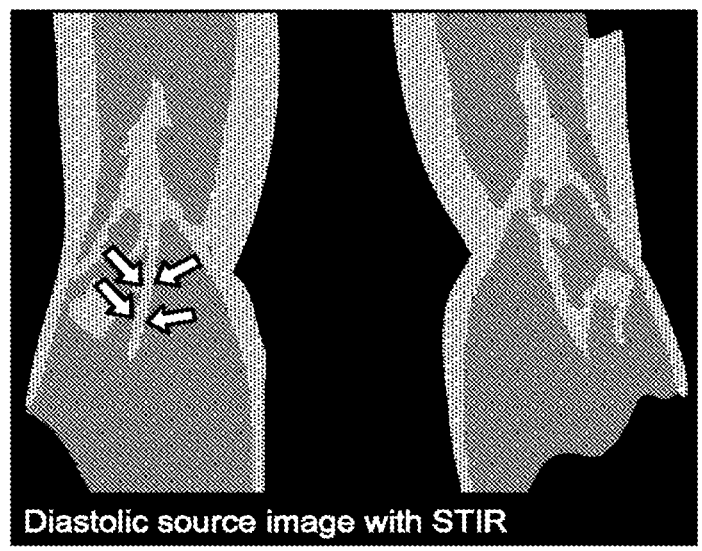
FIG. 2A, FIG. 2B, FIG. 2C and FIG. 2D are drawings illustrating a background of an embodiment.
Figure 2B:
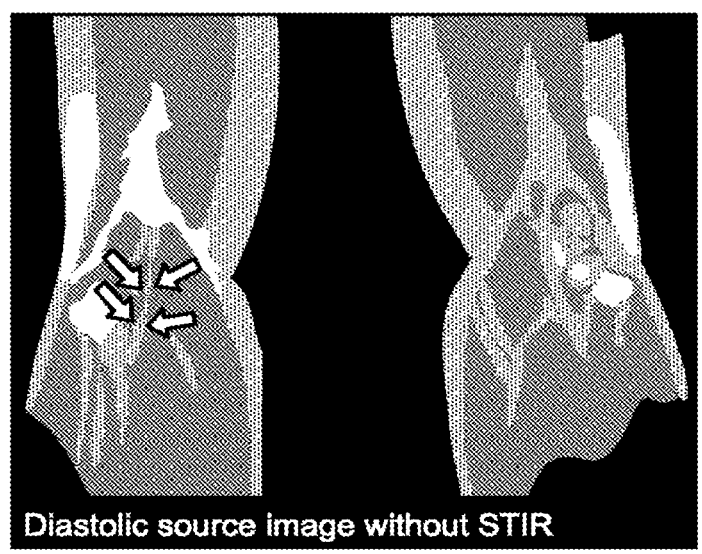
Figure 2C:
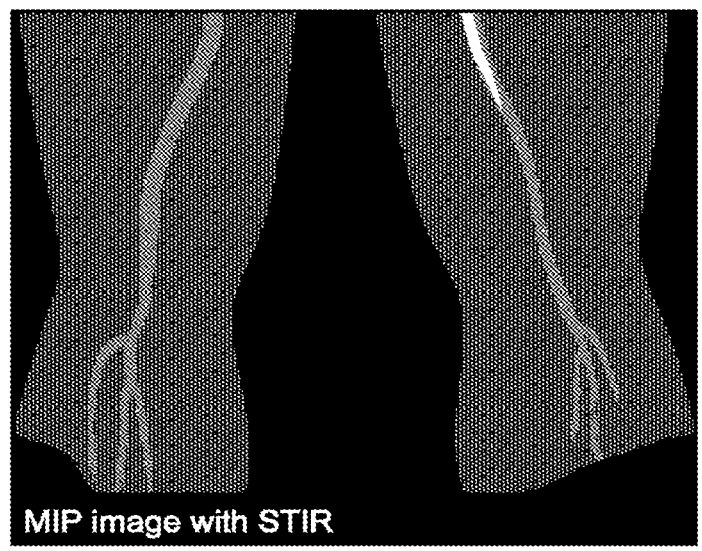
Figure 2D:
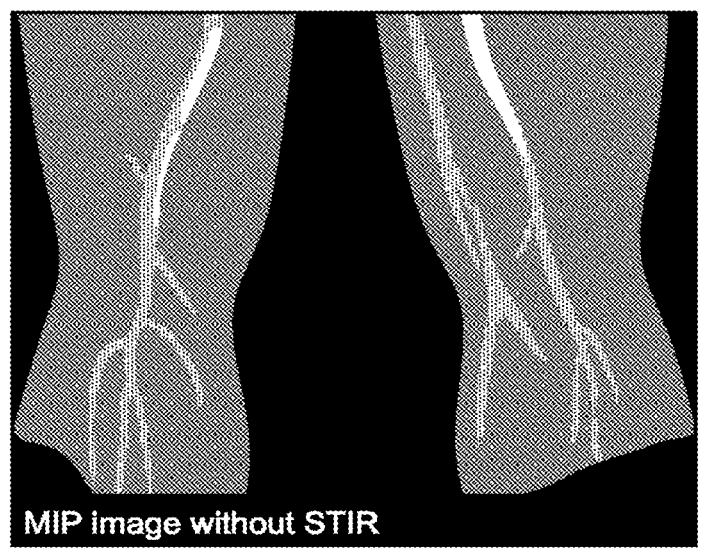

Each of FIG. 2A to FIG. 2D is an image generated by FBI method. FIG. 2A is a source image in which an STIR pulse is spatially non-selectively applied as the fat saturation pulse. FIG. 2B is a source image in which no fat saturation pulse is applied. FIG. 2C is a subtraction MIP image in which an STIR pulse is spatially non-selectively applied as the fat saturation pulse. FIG. 2D is a subtraction MIP image in which no fat saturation pulse is applied. In FIG. 2A and FIG. 2B, which are source images, signals of both tissues and blood vessels are depicted. On the other hand, in FIG. 2C and FIG. 2D, which are subtraction MIP images, only blood vessels are depicted.

Comparing FIG. 2A and FIG. 2C, in which fat saturation pulses are applied with FIG. 2B and FIG. 2D, in which no fat saturation is applied, in FIG. 2A and FIG. 2C, fat signals are suppressed. For example, if you compare the part indicated by the arrows in FIG. 2A with the part indicated by the arrows in FIG. 2B, blood vessel signals are more clearly depicted in FIG. 2A, compared to the case of FIG. 2B in which blood vessel signals are inconspicuous due to the lack of suppression of fat signals.

It is noted, however, that if an STIR pulse is spatially non-selectively applied as a fat saturation pulse, since blood in the upstream region is spatially non-selectively excited by the STIR pulse but the recovery of longitudinal magnetization is imperfect at the time of data acquisition, the overall blood signals become weak.

In view of this background, the magnetic resonance imaging apparatus 100 according to an embodiment includes the sequence control circuitry 120 and the processing circuitry 150. The sequence control circuitry 120 executes two pulse sequences, thereby acquiring two pieces of data, each of the two pulse sequences being a pulse sequence in which the sequence control circuitry acquires data after applying a short inversion time recovery (STIR) pulse while concurrently applying a gradient magnetic field for spatial selection and each of the two pulse sequences being executed in two different timings by the sequence control circuitry 120. The processing circuitry 150 generates, by the image generation function 136, an image by performing a subtraction processing between the two pieces of data acquired by the sequence control circuitry 120.

Figure 3:
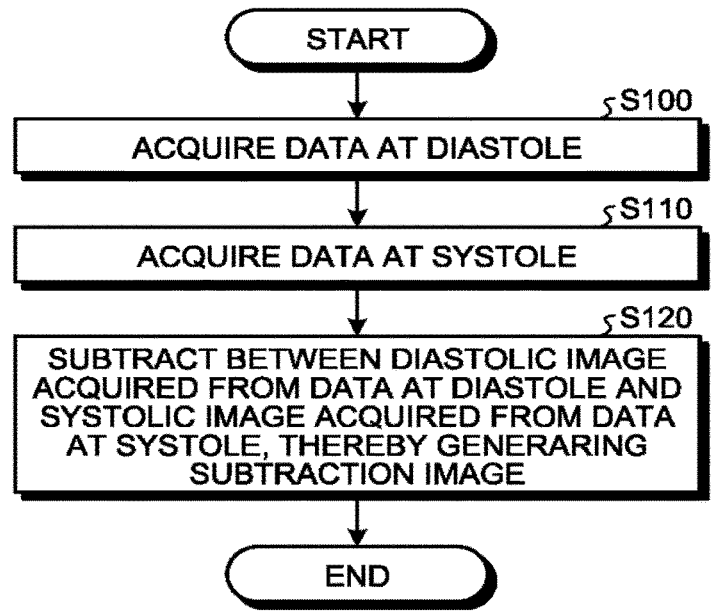
FIG. 3 is a flowchart illustrating the processing performed by a magnetic resonance imaging apparatus according to a first embodiment.
Figure 4:
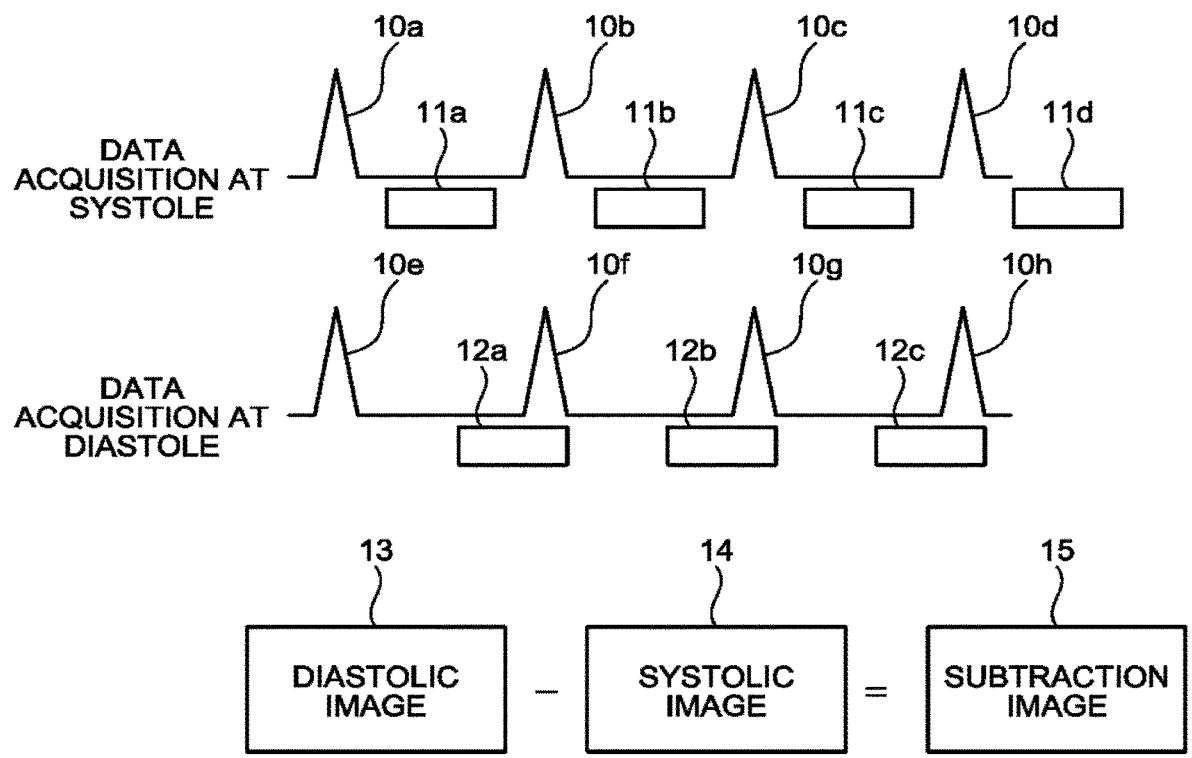
FIG. 4 is a diagram illustrating a pulse sequence executed by a magnetic resonance imaging apparatus according to the first embodiment.

With reference to FIG. 3 to FIG. 8, this situation is explained. FIG. 3 is a flowchart illustrating a processing performed by a magnetic resonance imaging apparatus 100 according to the first embodiment. In the first embodiment, the magnetic resonance imaging apparatus 100 performs an imaging using, for example, FBI method. In FBI method, data is acquired at two different timings, for example at two different cardiac phases. FIG. 4 is a diagram illustrating a pulse sequence executed by a magnetic resonance imaging apparatus 100 according to the first embodiment. FIG. 4 is a diagram illustrating a pulse sequence executed by a magnetic resonance imaging apparatus according to the first embodiment. The upper row of FIG. 4 indicates data acquisition in a systole. The horizontal direction indicates time. The second row of FIG. 4 indicates data acquisition in a diastole. The horizontal direction indicates time. The bottom row of FIG. 4 is a diagram explaining the subtraction processing in FBI method.

With reference to FIG. 4, using FIG. 3, processing performed by the magnetic resonance imaging apparatus according to the first embodiment is explained.

First of all, at Step S100, the sequence control circuitry 120 applies a pulse sequence to be described later in FIG. 5 to FIG. 7, thereby acquiring data at a diastolic cardiac phase. Specifically, as illustrated in the second row of FIG. 4, the sequence control circuitry 120 performs, at a diastolic cardiac phase, data acquisition 12a, 12b, 12c and the like, by applying a pulse sequence to be described in FIG. 5 to FIG. 7. The sequence control circuitry 120 performs each of the data acquisition 12a, 12b and 12c, by using each of R-waves 10e, 10f and 10g as a trigger, and by for example, electrocardiographic (ECG) gating, at a timing retarded from each trigger by a certain amount of time that corresponds to the diastolic cardiac phase.

Subsequently, at Step S110, the sequence control circuitry 120 applies a pulse sequence to be described later in FIG. 5 to FIG. 7, thereby acquiring data at systolic cardiac phase. Specifically, as illustrated in the top row of FIG. 4, the sequence control circuitry 120 performs, at a systolic cardiac phase, data acquisition 11a, 11b, 11c, 11d and the like, by applying a pulse sequence to be described in FIG. 5 to FIG. 7. The sequence control circuitry 120 performs each of the data acquisition 11a, 11b, 11c and 11d, by using each of R-waves 10a, 10b, 10c and 10d as a trigger, and by for example, electrocardiographic (ECG) gating, at a timing retarded from each trigger by a certain amount of time that corresponds to the systolic cardiac phase.

Based on the data acquisition 12a, 12b, 12c and the like performed by the sequence control circuitry 120 at Step S100, the processing circuitry 150 generates, by the image generation function 136, a diastolic image 13. Further, based on the data acquisition 11a, 11b, 11c, 11d and the like performed by the sequence control circuitry 120 at Step S110, the processing circuitry 150 generates, by the image generation function 136, a systolic image 14.

In this way, the sequence control circuitry 120 executes the pulse sequences to be described to be later in two different timings, for example, in two different cardiac phases, thereby acquiring two pieces of data that correspond to a piece of data corresponding to the diastolic image 13 and a piece of data corresponding to the systolic image 14.

Subsequently, at Step S120, the processing circuitry 150 performs, by the image generation function 136, a subtraction processing between the two pieces of data acquired at Step S100 and Step S110 by the sequence control circuitry 120, thereby generating an image. For example, as illustrated in the bottom row of FIG. 4, the processing circuitry 150 performs a subtraction processing between the diastolic image 13 acquired from data obtained by data acquisition 12a, 12b, 12c and the like at a diastole and the systolic image 14 acquired from data obtained by data acquisition 11a, 11b, 11c, 11d and the like at a systole, thereby generating, for example, a subtraction MIP image that is a subtraction image 15.

Next, with reference to FIG. 6 and FIG. 7, and by using FIG. 5, the details of the pulse sequences that the sequence control circuitry 120 executes in two different timings will be explained.

Figure 5:
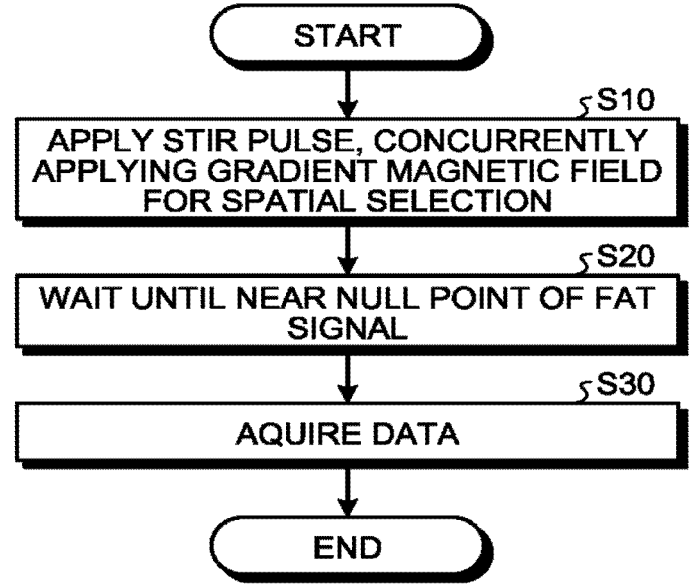
FIG. 5 is a flowchart illustrating a processing performed by a magnetic resonance imaging apparatus according to the first embodiment.

FIG. 5 is a flowchart illustrating a processing performed by a magnetic resonance imaging apparatus according to the first embodiment. Specifically, FIG. 5 is a flowchart illustrating an overall flow of each of pulse sequences that the sequence control circuitry 120 executes in each of the systole and the diastole. In other words, FIG. 5 represents an overall flow of a pulse sequence that the sequence control circuitry 120 executes at Step S100 and Step S110.

Figure 6:
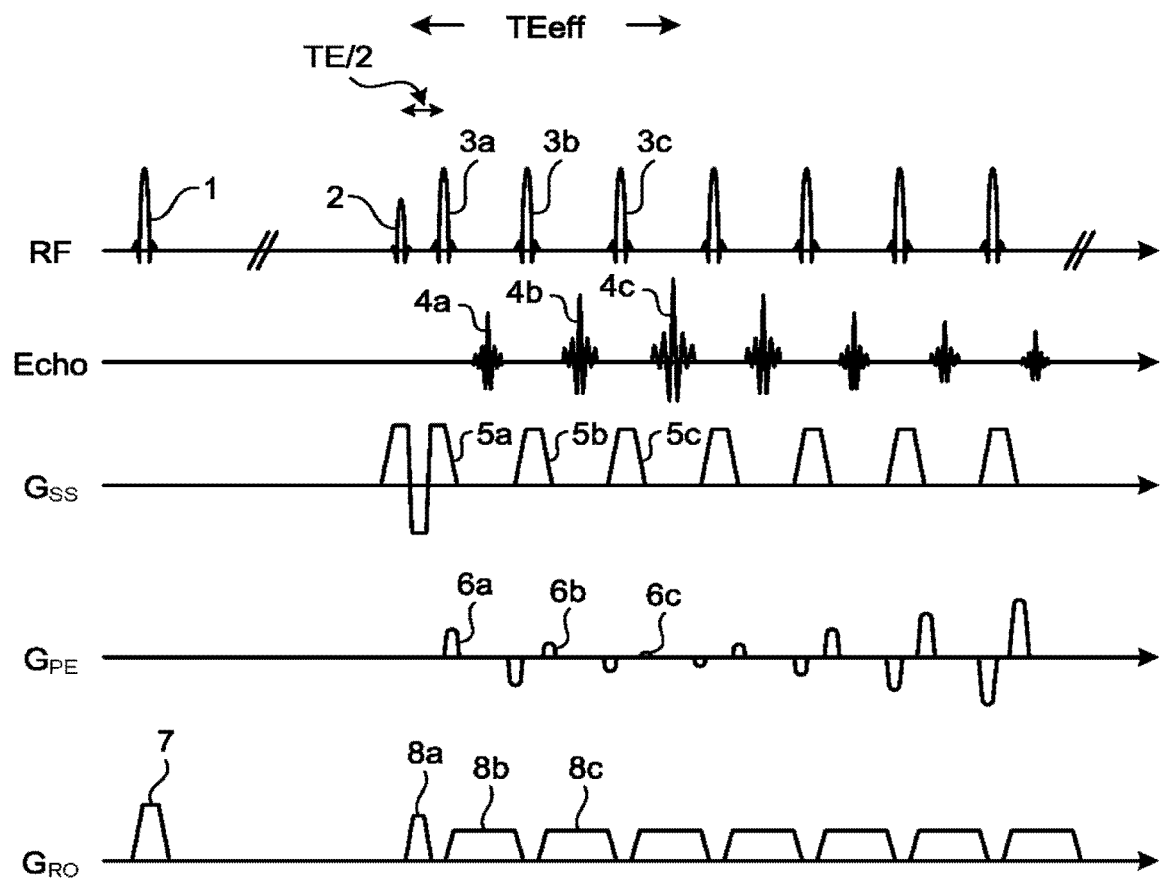
FIG. 6 is a diagram illustrating a pulse sequence executed by a magnetic resonance imaging apparatus according to the first embodiment.

Further, FIG. 6 is a diagram illustrating a pulse sequence executed by a magnetic resonance imaging apparatus according to the first embodiment. FIG. 6 is an example of a pulse sequence the sequence control circuitry 120 executes in FIG. 5. In FIG. 6, the horizontal axis indicates time. The top row of FIG. 6 indicates RF pulses applied. The second row of FIG. 6 indicates echoes generated by the RF pulses applied. Each of the third row, the fourth row, the fifth row of FIG. 6 indicates, respectively, a gradient magnetic field $G_{SS}$ in the slice direction, a gradient magnetic field $G_{PE}$ in the phase encode direction and a gradient magnetic field $G_{RO}$ in the readout direction.

In FIG. 5, first of all, at Step S10, the sequence control circuitry 120 applies an STIR pulse, while concurrently applying a gradient magnetic field for spatial selection. Specifically, as illustrated in FIG. 6, the sequence control circuitry 120 applies an STIR pulse 1, while concurrently applying a gradient magnetic field 7 that is the gradient magnetic field for spatial selection. The sequence control circuitry 120 applies, for example, the STIR pulse 1 whose flip angle is 180 degrees.

The STIR pulse 1 is an inversion pulse of relatively short inversion time (TI) designed to suppress fat signals. The sequence control circuitry 120 applies the STIR pulse 1. Here, the reason why it is possible to suppress fat signals by using the STIR pulse 1 that is an inversion pulse is the following: When the sequence control circuitry 120 applies the STIR pulse 1, the longitudinal magnetization of a tissue is inverted. Subsequently, the longitudinal magnetization of the tissue is relaxed according to the relaxation constant specific to the tissue, thereby reaching the so-called null point at which the longitudinal magnetization is zero, when a certain time has passed. If data is acquired near this null point, then the signal from the tissue is suppressed. Therefore, after the application of the STIR pulse 1 and at the null point in which the longitudinal magnetization of fat is substantially zero, if data acquisition 11*a*, 11*b*, 11*c*, 11*d*, 12*a*, 12*b*, 12*c*, and the like are performed, data acquisition in which fat signals are suppressed can be performed.

Next, the gradient magnetic field 7 that is a magnetic field for spatial selection will be explained.

First of all, let us assume a case in which the sequence control circuitry 120 does not concurrently apply a gradient magnetic field for spatial selection when applying the STIR pulse 1. In particular, for example, let us assume a case in which the sequence control circuitry 120 spatially non-selectively applies the STIR pulse 1. In such a case, as the STIR pulse 1 is spatially non-selectively applied, for example in a case in which blood vessel imaging is performed, blood that exists in the upstream region of the region of interest (ROI) in particular is unexpectedly excited by the STIR pulse 1. Consequently, in a case of an imaging condition in which TR is short, longitudinal magnetization of blood does not fully recover by the time of the start of data acquisition, which sometimes lowers the target blood signal intensity.

Thus, in the magnetic resonance imaging apparatus according to the first embodiment, in order to prevent blood that exists in the upstream region of the region of interest from being excited by the STIR pulse 1, the sequence control circuitry 120 applies, concurrently with the STIR pulse 1, a election gradient 7 that is the gradient magnetic field for spatial selection. For example, the sequence control circuitry 110 applies a selection gradient 7 that is a gradient magnetic field for spatial selection and that is a gradient magnetic field in which only tissues in the region of interest are excited by the STIR pulse 1.

Figure 7:
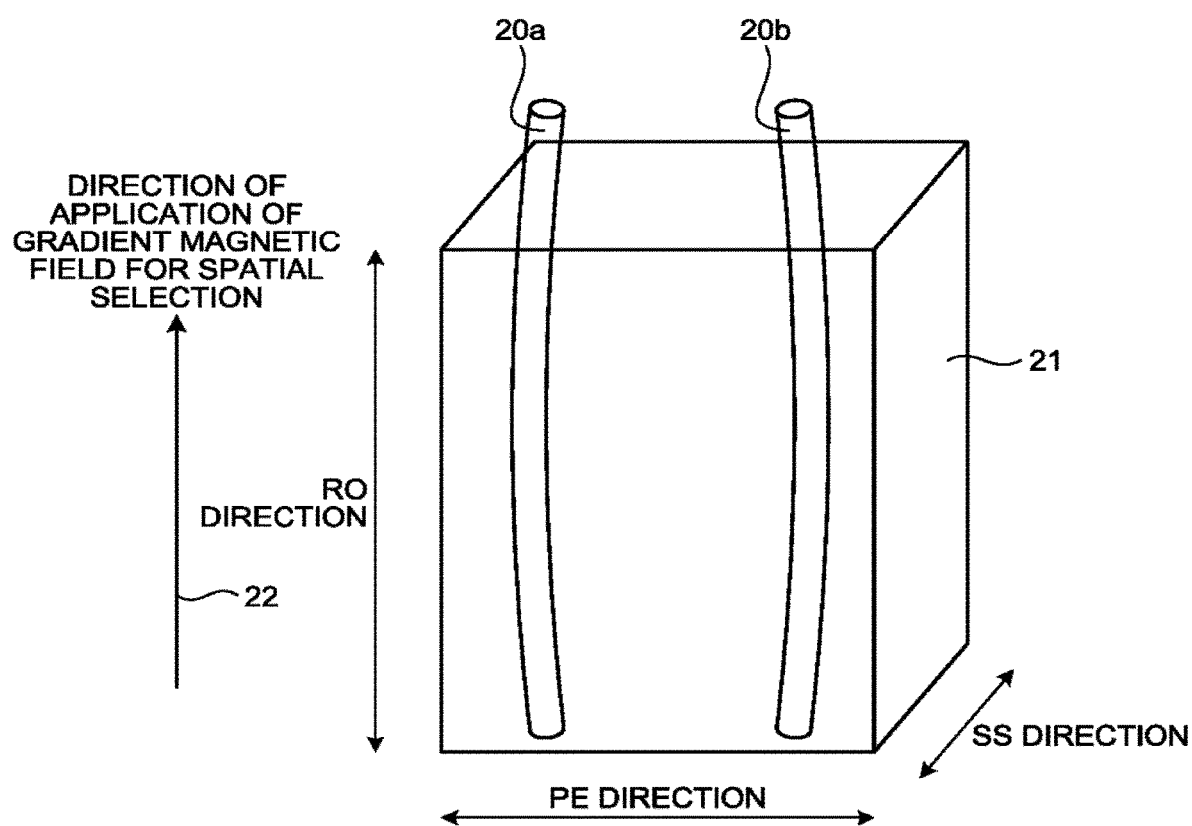
FIG. 7 is a drawing illustrating a processing performed by a magnetic resonance imaging apparatus according to the first embodiment.

FIG. 7 is a diagram illustrating a processing performed by a magnetic resonance imaging apparatus according to the first embodiment. More specifically, with reference to FIG. 7, the gradient magnetic field 7 that is the gradient magnetic field for spatial selection will be explained.

In FIG. 7, blood vessel 20*a* and blood vessel 20*b* indicate bloods vessels that exist in the region of interest and that are the object of the imaging. Each of the blood vessel 20*a* and the blood vessel 20*b* schematically indicates, for example, an artery and a vein in the lower extremities, respectively. In FIG. 7, an example of the slice selection (SS) direction, the phase encode (PE) direction and the readout direction is shown. In FBI method, the coronal imaging is the most common. Thus, as for the slice selection (SS) direction, anterior-posterior direction is selected. As for the phase encode (PE) direction, left-right direction is selected. As for the readout (RO) direction, the body-axial direction is selected.

The sequence control circuitry 120 applies the gradient magnetic field 7 that is the gradient magnetic field for spatial selection, in a way in which a plane perpendicular to the running direction of the blood vessel is selected. Here, for example, in the case of lower extremity imaging, the readout direction becomes the running direction of the blood vessel. Therefore, the sequence control circuitry 120 applies the gradient magnetic field that is the gradient magnetic field for spatial selection, in a way in which the plane perpendicular to the readout direction is selected. In other words, as illustrated in an arrow 22, the sequence control circuitry 120 determines that the application direction of the gradient magnetic field be the readout direction. In other words, the sequence control circuitry 120 applies an STIR pulse while concurrently applying the gradient magnetic field 7 in the readout direction that is the magnetic field for spatial selection. It is noted that, in the above-described example, since a case of the lower extremities imaging is explained, the application direction of the magnetic field 7 that is the gradient magnetic field for spatial selection is determined to be the readout direction. However, the application direction of the gradient magnetic field 7 may be other than the readout direction, depending on the imaging target or the purpose of the imaging.

Here, the reason why the sequence control circuitry 120 applies the gradient magnetic field 7 that is the magnetic field for spatial selection in a way in which the plane perpendicular to the running direction of the blood vessel is selected is the following: Let us assume that the sequence control circuitry 120 were to apply the gradient magnetic field 7 that is the gradient magnetic field for spatial selection in a way in which a plane parallel to the running direction of the blood vessel is selected. In this case, since the plane selected and the running direction of the blood vessel is parallel, blood of blood vessels outside the region of interest (especially blood that is outside the region of interest and that is in the upstream side in which the blood flows into the region of interest at the time of data acquisition) would be excited, which may lead to the weakening of blood signals. Thus, the sequence control circuitry 120 applies the magnetic field 7 that is a magnetic field for spatial selection, selecting a plane of the direction with the minimum amount of blood in the upstream region entering into the region of interest at the time of data acquisition.

In FIG. 7, the spatial region excited by the STIR pulse 1 selected by the gradient magnetic field 7 that is the gradient magnetic field for spatial selection is illustrated as a region 21. The sequence control circuitry 120 applies the gradient magnetic field 7 with the intensity that the region 21 is substantially the same with the region of interest.

Returning to FIG. 5, at Step S20, the sequence control circuitry 120 waits until near the null point of fat signals.

Subsequently, at Step S30, the sequence control circuitry 120 acquires data acquisition. It is noted that, in the first embodiment, as data acquisition executed at Step S30, as illustrated in FIG. 6, a case is explained in which half-Fourier FSE (Fast Spin Echo) method is employed.

As illustrated in FIG. 6, the sequence control circuitry 120 applies an RF pulse 2 of a flip-angle of 90 degrees, in the beginning of data acquisition sequence. After the half of the echo time (TE) passed, an RF pulse 3*a* of a flip angle of 180 degrees is applied. The sequence control circuitry 120 sequentially applies, for each TE from then on, an RF pulse 3*b*, 3*c* or the like of a flip angle of 180 degrees Thus, echoes 4*a*, 4*b*, 4*c* and the like are generated. Further, the sequence control circuitry 120 applies gradient magnetic fields 5*a*, 5*b* and the slice direction. Further, the sequence control circuitry 120 applies gradient magnetic fields 6*a*, 6*b* and 6*c* in the phase encode direction, thereby executing phase encoding. Further, the sequence control circuitry 120 applies a gradient magnetic field 8*a* in the readout direction. The sequence control circuitry 120 applies gradient magnetic fields 8*b* and 8*c* in the readout direction while echoes are being generated, thereby acquiring data. In this way, data is acquired while fat signals are being suppressed.

It is noted that, as a pulse sequence executed at step S30, the pulse sequence may be two-dimensional pulse sequence or three-dimensional pulse sequence. Further, as for the pulse sequence executed at Step S30 at FIG. 7, aside from FASE (Fast Asymmetric SE) method, EPI (Echo Planar Imaging) method, and FSE (Fast Spin Echo) method, or other pulse sequences of Spin Echo Method and the like, many pulse sequences are possible.

Figure 8:
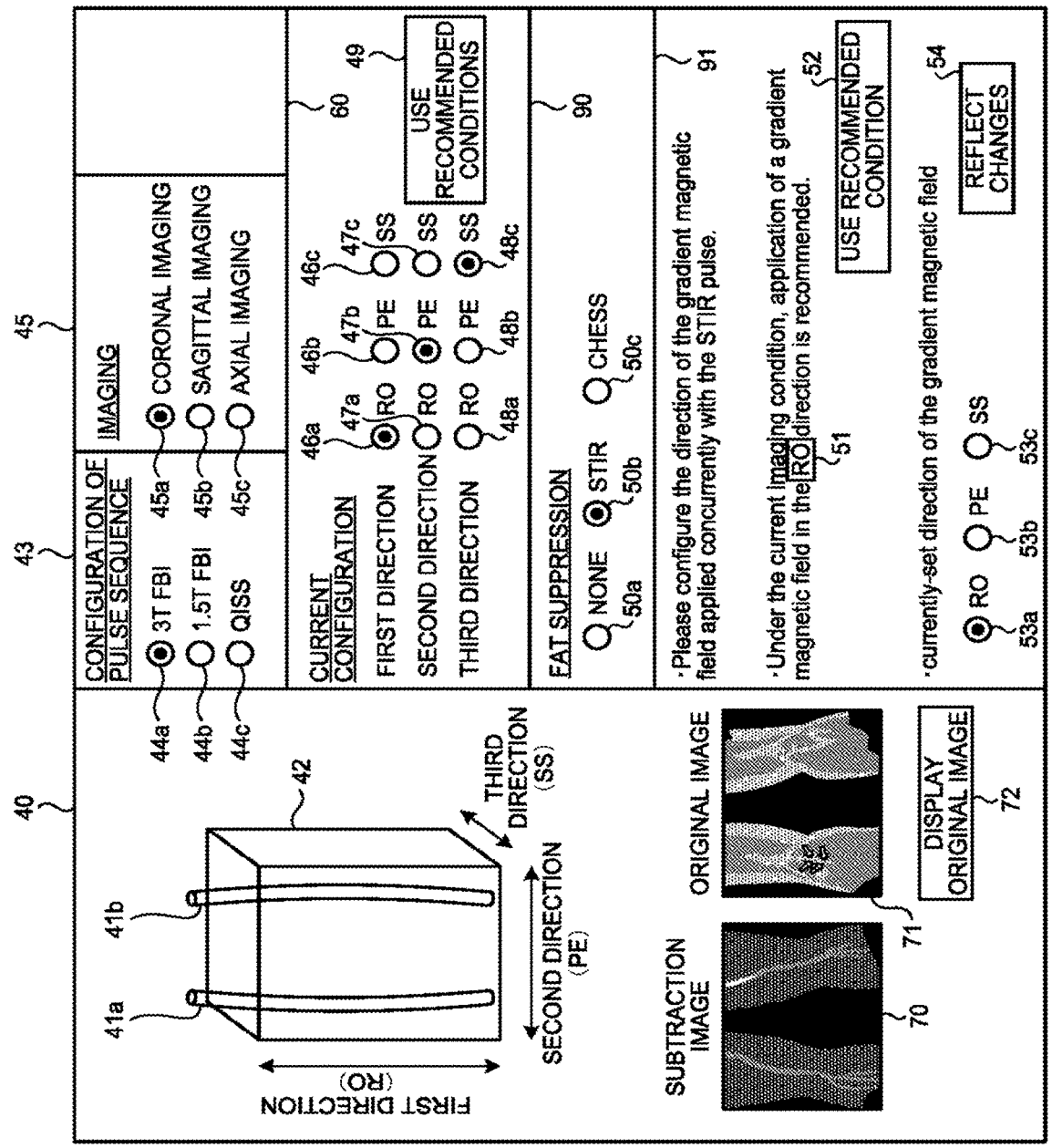
FIG. 8 is a drawing illustrating a graphical user interface (GUI) corresponding to a magnetic resonance imaging apparatus according to the first embodiment.

With reference to FIG. 8, an example of a GUI employed in the magnetic resonance imaging apparatus 100 according to the first embodiment will be explained. FIG. 8 is a diagram illustrating an example of a GUI according to a magnetic resonance imaging apparatus according to the first embodiment.

The processing circuitry 150 causes the display 135 to present, on a panel 40 of the display 135, by the control function 133, an image obtained. For example, the processing circuitry 150 causes the display 135 to present, by the control function 133, a subtraction image 70 generated at Step S120. For example, the processing circuitry 150 causes the display 135 to present, on the panel 40 of the display 135, by the control function 133, a subtraction image 70 generated at Step S120.

Further, when a user clicks a button 72, the processing circuitry 150 causes the display 135 to present, on the panel 40 of the display 135, by the control function 133, a source image 71 (for example, at least one of the diastolic image 13 and the systolic image 14 that are two pieces of data in which the subtraction processing has not yet been performed.) By doing this, if a disease such as stenosis is found in the subtraction image 70 and a situation in which it is desirable for a user to see the source image 71 such as the diastolic image 13, the systolic image 14 and the like arises, the processing circuitry 150 causes the display 135 to present a source image 71 on which fat suppression is performed.

Further, the processing circuitry 150 causes the display 135 to present, by the control function 133, the region 21, which is the region excited by the STIR pulse 1 selected by the gradient magnetic field 7 that is the gradient fief for spatial selection, as a region 42 on the panel 40 of the display 135. The region 21 is superimposed on blood vessels 41a and 41b. Further, the processing circuitry 150 may cause the display 135 to present, by the control function 133, the relationship between the first direction, the second direction and the third direction that are directions designated by the physical location of the imaging target and the readout (RO) direction, the phase encode (PE) direction and the slice selection (SS) direction in the pulse sequence. In the example of FIG. 8, the first direction that is the body-axial direction corresponds to the readout (RO) direction. The second direction that is the left-right direction corresponds to the phase encode (PE) direction. The third direction that is the anterior-posterior direction corresponds to the slice selection (SS) direction. Further, the processing circuitry 150 may, by the control function 133, further superimpose and display the region of interest on the region 42.

Further, the processing circuitry 150 accepts, by the control function 133, by buttons 44a, 44b, 44c and the like on a panel 43, a change of the configuration of the pulse sequence executed by the sequence control circuitry 120. Further, the processing circuitry 150 accepts, by the control function 133, a change of an imaging condition executed by the sequence control circuitry 120, by the control function 133, by buttons 45a, 45b, 45c and the like on a panel 45.

Further, the processing circuitry 150 accepts, by the control function 133, by buttons 46a, 46b, 46c, 47a, 47b, 47c, 48a, 48b, 48c and the like on a panel 60, a change of the readout (RO) direction, the phase encode (PE) direction and the slice selection (SS) direction. For example, in a case in which a user chooses the phase encode (PE) direction as the first direction that is the body-axis direction, the slice selection (SS) direction as the second direction that is the left-right direction and the readout (RO) direction as the third direction that is the anterior-posterior direction, the user selects the button 46b, the button 47c and the button 48a. Further, if the user selects a button 49, conditions determined based on the body part to be imaged, imaging method, imaging method, information of the pulse sequence is automatically set.

Further, the processing circuitry 150 accepts, from a user, by the control function 133, by buttons 50a, 50b and 50c on a panel 90 whether or not a fat saturation pulse is applied, an input of the kind of the fat saturation pulse applied, and the like.

Further, the processing circuitry 150 accepts, from a user, by the control function 133, by buttons 53a, 53b, 53c and 54, on a panel 91, an input of a direction of the gradient magnetic field for spatial selection concurrently applied with the STIR pulse 1 by the sequence control circuitry 120. For example, in a case in which a user clicks the button 54 after the user selects the button 53b, the processing circuitry 150 accepts, by the control function 133, an input requesting that the direction of the gradient magnetic field concurrently applied with the STIR pulse 1 be the phase encode (PE) direction. The sequence control circuitry 120 applies the gradient magnetic field in the direction corresponding to the input accepted, concurrently with the STIR pulse 1, based on the result of the input accepted.

It is noted that the processing circuitry 150 may automatically calculate, by the control function 133, the direction of the gradient magnetic field for spatial selection that is concurrently applied with the STIR pulse 1 by the sequence control circuitry 120, based on a body part of the imaging, the imaging method or information of the pulse sequence employed.

Further, the processing circuitry 150 may calculate, by the control function 133, a recommended direction of a gradient magnetic field for spatial selection that is concurrently applied with the STIR pulse 1 by the sequence control circuitry 12 based on the body part of the imaging, the imaging method or the information of the pulse sequence employed. Further, the processing circuitry 150 may cause the display 135 to present the direction calculated to a display area 51. Further, the processing circuitry 150 may accept, by the control function 133, from a user, by a button 52, an input requesting that the recommended condition calculated be used. When the processing circuitry 150 accepts the input requesting that the recommended condition calculated be used, the sequence control circuitry 120 may apply a gradient magnetic field in the recommended direction.

As described above, according to the first embodiment, fat signals can be suppressed effectively.

It is noted that embodiments are not limited to this example.

For example, the flip angle of the STIR pulse 1 applied by the sequence control circuitry 120 is not limited to 90 degrees. The flip angle may be less than 90 degrees or larger than 90 degrees.

In FIG. 4, the order of execution of Step S100 and Step S110 is not limited to the order that is illustrated. For example, the order of execution of Step S100 and Step S110 may be swapped. In other words, the sequence control circuitry 120 may acquire data at a diastole after acquiring data at a systole. Further, the sequence control circuitry 120 may execute Step S100 and Step S110 concurrently.

In FIG. 4, as an example of two different cardiac phases, a case of two cardiac phases of the diastole and the systole is explained. However, embodiments are not limited to this. As another example of the two different cardiac phases, two arbitrary cardiac phases other than the diastole and the systole may be selected.

Further, at Step S120, the processing executed by the processing circuitry 150 need not be the simple subtraction processing. For example, the processing may be a weighted subtraction or other methods.

Further, the sequence control circuitry 120 may acquire data for equal to or more than three cardiac phases, thereby acquiring equal to or more than three pieces of data. The processing circuitry 150 may generate an image, by the image generating function 136, based on the equal to or more than three pieces of data acquired.

Further, in the embodiment, a case is explained in which the sequence control circuitry 120 executes the pulse sequences in different cardiac phases using ECG gating. However, the sequence control circuitry 120 may execute the pulse sequences in synchronization with pulsation.

Second Embodiment

In the first embodiment, a case is explained in which fat suppression by FBI method, a non-contrast pulse sequence that performs subtraction processing. In the second embodiment, with reference to FIG. 10 and FIG. 11, using FIG. 9, a case will be explained in which fat suppression by quiescent interval single shot (QISS) method. QISS method is a method in which it is possible to depict peripheral blood vessels easily and quickly without infusing a contrast agent. No subtraction processing of images is necessary in QISS method, thus for example, QISS method has an advantage that it is robust against body movement during the examination. Further, in QISS method, it is possible to acquire data of one slice at one heartbeat at the shortest, so it becomes possible to shorten the time of the examination.

FIG. 9 is a flowchart illustrating a processing performed by a magnetic resonance imaging apparatus according to the second embodiment. FIG. 10 is a diagram illustrating a pulse sequence executed by a magnetic resonance imaging apparatus according to the second embodiment. The top row of FIG. 10 indicates heartbeats. An R-wave 30a and an R-wave 30b indicates R-waves. The second row of FIG. 10 indicates RF pulses applied by the sequence control circuitry 120 and data acquisition. The third row of FIG. 10 indicates a gradient magnetic field for spatial selection concurrently applied with the fat saturation pulse.

First of all, at Step S200, the sequence control circuitry 120 applies a first saturation pulse 31 when a certain time has passed since the R-wave 30a, that is, for example, when about 100 msec has passed. The sequence control circuitry 120, for example, spatially selectively applies the first saturation pulse 31. The region selected by the first saturation pulse 31 is a region substantially the same with the imaging region (the imaging slice).

Next, at Step S210, the sequence control circuitry 120 applies a venous saturation pulse. For example, the sequence control circuitry 120 spatially selectively applies a venous saturation pulse 32 including a venous upstream region with respect to the imaging region.

Next, the sequence control circuitry 120 waits until fresh arterial blood flows into the imaging region and until a diastole that is suitable for data acquisition. This interval is called quiescent interval (QI interval).

Next, at Step S220, the sequence control circuitry applies a frequency-selective fat saturation pulse 33 while concurrently applying a gradient magnetic field 35 for spatial selection. An example of the frequency-selective fat saturation pulse 33 includes a chemical shift selective (CHESS) pulse. An example of the flip angle of the frequency-selective fat saturation pulse 33 is 90 degrees. However, embodiments are not limited to this example. The flip angle may be larger than 90 degrees, or may be smaller than 90 degrees.

Figure 11:
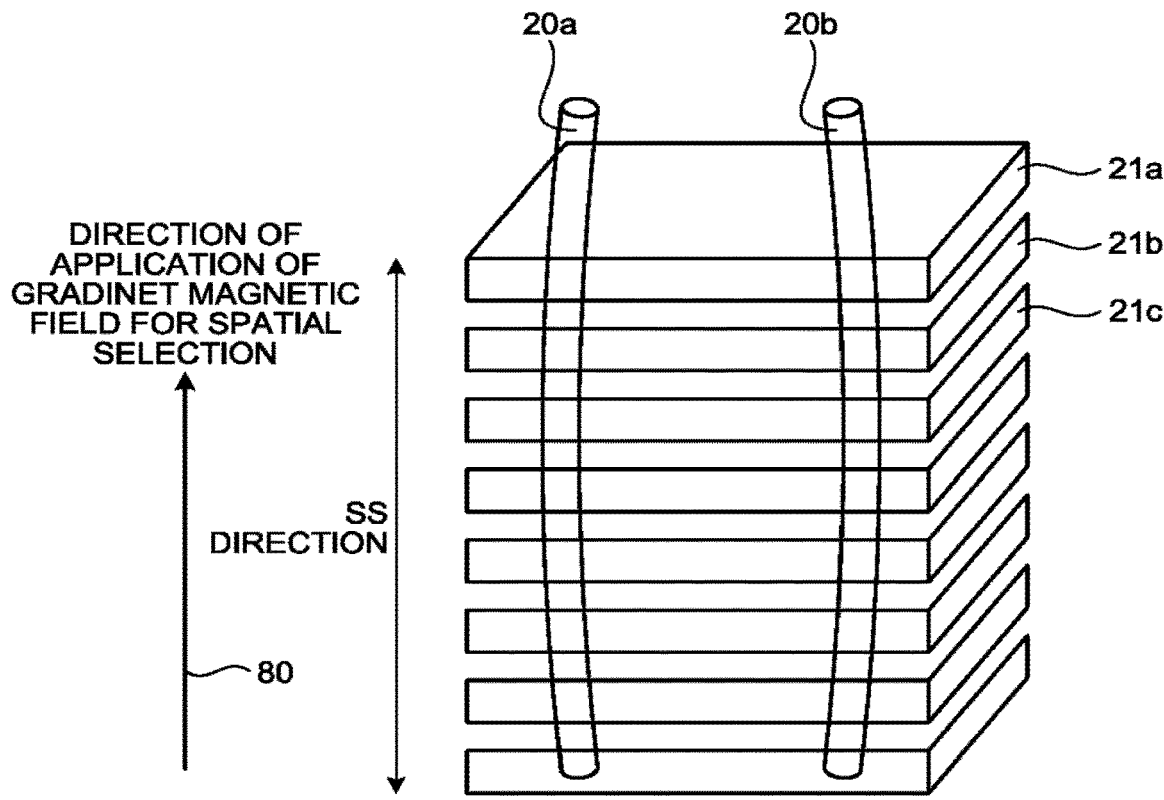
FIG. 11 is a drawing illustrating a processing performed by a magnetic resonance imaging apparatus according to the second embodiment.

FIG. 11 is a drawing illustrating a processing performed by a magnetic resonance imaging apparatus according to the second embodiment. With reference to FIG. 11, the gradient magnetic field 35 for spatial selection is explained.

A blood vessel 20a and a blood vessel 20b indicate blood vessels.

Each of a region 21a, a region 21b and a region 21c indicates a single slice in which one data acquisition is performed. In QISS, for example, for each R-R interval, one slice of acquisition is performed at maximum. In other words, the region 21a is a region in which, for example, data is acquired by the data acquisition from the R-wave 30a to the R-wave 30b. For each single heartbeat, data is acquired, such as the region 21b and the region 21c.

Therefore, for example, the body axial direction (the up and down direction of the figure) becomes the slice selection (SS) direction.

Thus, also in QISS, in order not excite the upstream blood, as shown in the arrow 80, the sequence control circuitry 120 applies the frequency-selective fat saturation pulse 33, while concurrently applying the gradient magnetic field 35 that is for spatial selection so that the plane perpendicular to the running direction of the blood vessel is to be selected. The direction of the gradient magnetic field in which the plane perpendicular to the running direction of the blood vessel is to be selected becomes, for example, slice selection (SS) direction. The sequence control circuitry 120 applies the gradient magnetic field 35 for spatial selection, for example, in the slice selection (SS) direction.

Next, at Step S230, the sequence control circuitry 120 executes a balanced steady-state free precession (bSSFP) sequence 34, thereby acquiring data. The processing circuitry 150 generates, by the image generation function 136, data acquired by the sequence control circuitry 120.

As described above, in the second embodiment, in QISS method, fat signal is effectively suppressed.

Third Embodiment

In the third embodiment, similarly to the case of the second embodiment, QISS method is employed for fat suppression. In the third embodiment, in contrast with the second embodiment in which a frequency selective fat saturation pulse is applied, an STIR pulse is employed similarly to the case of the first embodiment.

Figure 12:
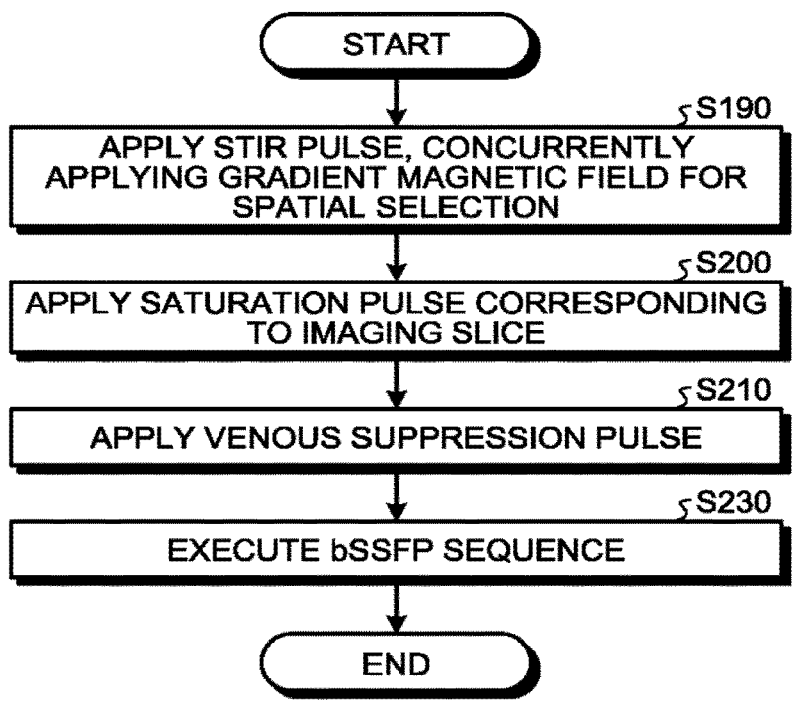
FIG. 12 is a flowchart illustrating a processing performed by a magnetic resonance imaging apparatus according to the third embodiment.
Figure 13:
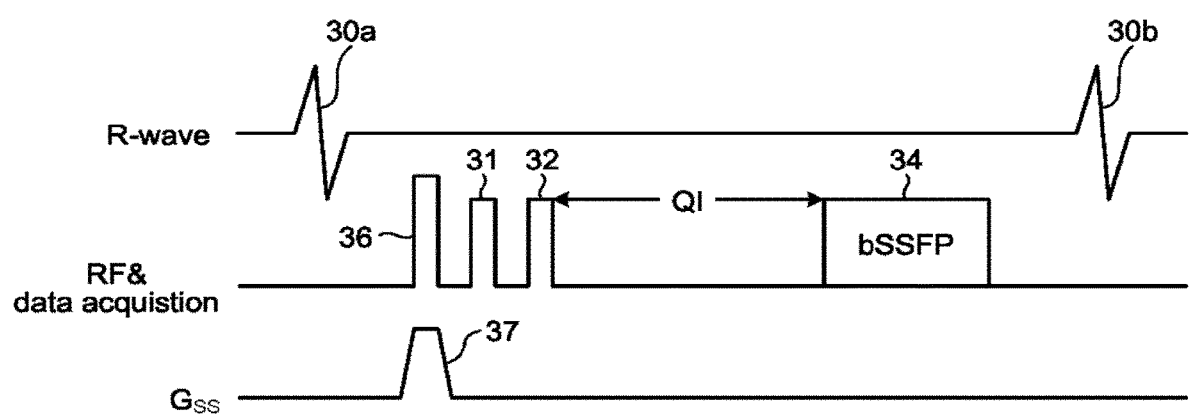
FIG. 13 is a diagram illustrating a pulse sequence executed by a magnetic resonance imaging apparatus according to the third embodiment.

With reference to FIG. 12 and FIG. 13, the third embodiment is explained. FIG. 12 is a flowchart illustrating a processing performed by a magnetic resonance imaging apparatus according to the third embodiment. FIG. 13 is a diagram illustrating a pulse sequence executed by a magnetic resonance imaging apparatus according to the third embodiment. The top row of FIG. 13 indicates heartbeats. R-wave 30a and R-wave 30b represent R-waves. The second row of FIG. 13 indicates RF pulses applied by the sequence control circuitry 120 and data acquisition. The third row of FIG. 13 indicates the gradient magnetic field for spatial selection that is applied concurrently with a fat saturation pulse.

First of all, at Step S190, the sequence control circuitry 120 applies an STIR pulse 36, while concurrently applying a gradient magnetic field 37 for spatial selection.

Subsequently, at Step S200, the sequence control circuitry 120 applies, similarly to the case of the second embodiment, a first saturation pulse 31 that is a first RF pulse corresponding to the imaging slice.

Subsequently, at Step S210, the sequence control circuitry 120 applies, similarly to the case of the second embodiment, a saturation pulse 32. The saturation pulse 32 is a second RE pulse that is an RF pulse for venous signal suppression.

Subsequently, at Step S230, when the QI interval has passed, the sequence control circuitry 120 acquires data by a bSSFP sequence 34.

The processing circuitry 150 generates an image based on the data acquired by the sequence control circuitry 120.

Other Embodiments

Embodiments are not limited to the case described above. For example, in the FBI method of the embodiments, in the case of flow-dephasing or flow spoiling, the sequence control circuitry 120 may apply a readout (RO) spoiler at a systole while applying no readout spoiler at a diastole so as not to spoil the diastolic signal.

Further, in the FBI method of the embodiments, in the case of performing flow compensation, the sequence control circuitry 120 may perform diastolic acquisition with readout (RO) flow compensation at a diastole in order to increase the signal while performing systolic acquisition without readout (RO) flow compensation at a systole in order to lower the signal.

It is noted that the method described above may be applicable to a simple FBI method alone, regardless of whether or not to apply an STIR pulse.

Computer Programs

Further, the instructions presented in the processing procedures described in the above embodiments may be executed according to a computer program (hereinafter, "program") that is software. It is possible to achieve the same advantageous effects as those from the magnetic resonance imaging apparatus 100 in the above embodiments, by causing a general-purpose computer to store the program therein in advance and to read the program. The instructions described in the above embodiments are recorded as a computer-executable program onto a magnetic disk (e.g., a flexible disk, a hard disk), an optical disc (e.g., a Compact Disc Read-Only Memory [CD-ROM], a Compact Disc Recordable [CD-R], a Compact Disc Rewritable [CD-RW], a Digital Versatile Disk Read-Only Memory [DVD-ROM], a Digital Versatile Disk Recordable [DVD±R], a Digital Versatile Disk Rewritable [DVD±RW]), a semiconductor memory, or the like. Any storage format can be used, as long as computer or an incorporated system is able to read data from the storage medium. The computer is able to realize the same operations as those performed by the magnetic resonance imaging apparatus 100 described in the above embodiments, by reading the program from the recording medium and having the CPU execute the instructions written in the program according to the read program. Further, when obtaining or reading the program, the computer may obtain or read the program via a network.

Further, according to the instructions in the program installed from the storage medium into the computer or the incorporated system, an Operating System (OS) working in the computer, middleware (MW) such as database management software or a network may execute a part of the processes performed for realizing the embodiments described above. Further, the storage medium does not necessarily have to a medium that is independent of the computer or the incorporated system. The storage medium may be such a storage medium that stores therein or temporarily stores therein the downloaded program transferred via a Local Area Network (LAN), the Internet, or the like. Further, the storage medium does not necessarily have to be one. Even the situation where the processes described in the above embodiments are executed from a plurality of media is included in possible modes of the storage medium implementing the embodiments. The medium/media may have any configuration.

Further, the computer or the incorporated system used in any of the embodiments is configured to execute the processes described in the above embodiments according to the program stored in the storage medium. The computer or the incorporated system may be configured by using a single apparatus such as a personal computer or a microcomputer or may be configured by using a system in which a plurality of apparatuses are connected together via a network. Furthermore, the computer used in any of the embodiments does not necessarily have to be a personal computer and may be an arithmetic processing apparatus, a microcomputer, or the like included in an information processing device. The term "computer" generally refers to any device or apparatus that is capable of realizing the functions described in the embodiments by using the program.

A Hardware Configuration

Figure 14:
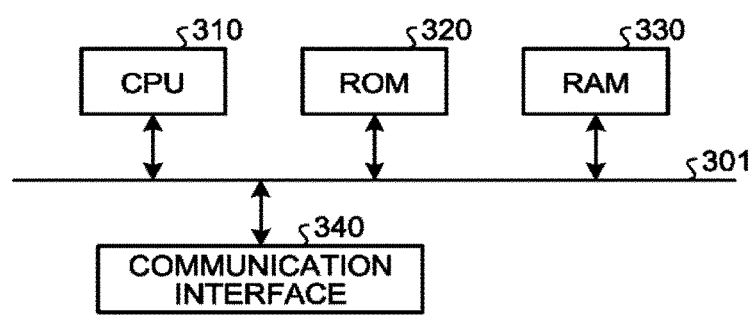
FIG. 14 is a drawing illustrating a hardware configuration of an image processing apparatus according to an embodiment.

FIG. 14 is a diagram of a hardware configuration of a computer 130 (image processing apparatus) according to an embodiment. The image processing apparatus according to the embodiments described above includes a controlling device such as a Central Processing Unit (CPU) 310, storage devices such as a Read-Only Memory (ROM) 320 and a Random Access Memory (RAM) 330, a communication interface (I/F) 340 that connects to a network and performs communication, and a bus 301 that connects the units together.

The program executed by the image processing apparatus according to the embodiments described above is provided as being incorporated, in advance, in the ROM 320 or the like. Further, the program executed by the image processing apparatus according to the embodiments described above is able to cause the computer to function as the units of the image processing apparatus described above. The computer is configured so that the CPU 310 is able to read the program from a computer-readable storage medium into a main storage device and to execute the read program.

According to a magnetic resonance imaging apparatus and a magnetic resonance imaging method, it becomes possible to effectively suppress fat signals.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus, comprising:
sequence control circuitry configured to execute two pulse sequences, thereby acquiring two pieces of data, each of the two pulse sequences being a pulse sequence in which the sequence control circuitry acquires data after applying a short inversion time recovery (STIR) pulse while concurrently applying a gradient magnetic field for spatial selection and each of the two pulse sequences being executed in two different timings by the sequence control circuitry; and processing circuitry configured to generate an image by performing a subtraction processing between the two pieces of data acquired by the sequence control circuitry, wherein the sequence control circuitry is configured to apply the STIR pulse while concurrently applying the gradient magnetic field in a way in which a plane perpendicular to a running direction of a blood vessel is selected.

2. The magnetic resonance imaging apparatus according to claim 1, wherein the sequence control circuitry is configured to apply the STIR pulse while concurrently applying the gradient magnetic field in a readout direction.

3. The magnetic resonance imaging apparatus according to claim 1, wherein the processing circuitry is configured to accept, from a user, an input of a direction of the gradient magnetic field applied and the sequence control circuitry is configured to apply the gradient magnetic field based on a result of the input accepted.

4. The magnetic resonance imaging apparatus according to claim 1, wherein the processing circuitry is configured to cause a display to present at least one of the two pieces of data that are pieces of data in which the subtraction processing has not yet been performed.

5. A magnetic resonance imaging method executed in a magnetic resonance imaging apparatus, including:

executing, by sequence control circuitry, two pulse sequences, each of the two pulse sequences being a pulse sequence in which the sequence control circuitry acquires data after applying a short inversion time recovery (STIR) pulse while concurrently applying a gradient magnetic field for spatial selection and each of the two pulse sequences being executed in two different timings by the sequence control circuitry; and acquiring, by the sequence control circuitry, two pieces of data;

generating, by processing circuitry, an image, by performing a subtraction processing between the two pieces of data acquired by the sequence control circuitry, and applying the STIR pulse while concurrently applying the gradient magnetic field in a way in which a plane perpendicular to a running direction of a blood vessel is selected.

* * * * *